US011052166B1

United States Patent
Graham, Jr. et al.

(10) Patent No.: US 11,052,166 B1
(45) Date of Patent: Jul. 6, 2021

(54) FREQUENCY SELECTIVE VIRAL INACTIVATION THROUGH BOND BREAKING

(71) Applicants: James Arthur Graham, Jr., Chicago, IL (US); Ghobad Heidari-Bateni, San Diego, CA (US); Stanton C Braden, San Diego, CA (US); Craig Martin Gregersen, Apple Valley, MN (US)

(72) Inventors: James Arthur Graham, Jr., Chicago, IL (US); Ghobad Heidari-Bateni, San Diego, CA (US); Stanton C Braden, San Diego, CA (US); Craig Martin Gregersen, Apple Valley, MN (US)

( * ) Notice: Subject to any disclaimer, the term of this patent is extended or adjusted under 35 U.S.C. 154(b) by 0 days.

(21) Appl. No.: 16/927,917

(22) Filed: Jul. 13, 2020

Related U.S. Application Data

(60) Provisional application No. 63/050,458, filed on Jul. 10, 2020.

(51) Int. Cl.
| | |
|---|---|
| *A61L 2/10* | (2006.01) |
| *A61L 2/08* | (2006.01) |
| *A61L 2/26* | (2006.01) |
| *A61L 2/24* | (2006.01) |

(52) U.S. Cl.
CPC ............... *A61L 2/085* (2013.01); *A61L 2/10* (2013.01); *A61L 2/24* (2013.01); *A61L 2/26* (2013.01); *A61L 2202/14* (2013.01); *A61L 2202/16* (2013.01)

(58) Field of Classification Search
CPC .................................. A61L 2/085; A61L 2/10
See application file for complete search history.

(56) References Cited

U.S. PATENT DOCUMENTS

| 6,165,526 A | * | 12/2000 | Newman | ............... A23L 3/0055 422/24 |
|---|---|---|---|---|
| 2016/0355411 A1 | * | 12/2016 | Fahs, II | .................. C02F 1/325 |
| 2017/0112954 A1 | * | 4/2017 | Dayton | ...................... A61L 2/10 |
| 2019/0099509 A1 | * | 4/2019 | Martz | ........................ A61L 2/10 |
| 2019/0328598 A1 | * | 10/2019 | Mangiardi | ............. A47B 96/00 |

OTHER PUBLICATIONS

Poole, Ian, Radio Waves and the Ionosphere, American Radio Relay League (ARRL), Nov. 1999,QST, https://www.arrl.org/files/file/Technology/pdf/119962.pdf.
Kampf, Günter & Voss, Andreas & Scheithauer, Simone. (2020). Inactivation of Coronaviruses by Heat. Journal of Hospital Infection, https://doi.org/10.1016/j.jhin.2020.03.025.

* cited by examiner

Primary Examiner — Donald R Spamer

(57) ABSTRACT

An apparatus is provided for delivering IR and/or UV radiation, to an area or a surface in which virions, such as SARS-CoV-2 (the virus that causes the disease, COVID-19), may exist, wherein the IR radiation is intended to degrade the viral envelope of the virions and wherein the UV radiation is intended to break specific molecular bonds in order to degrade the RNA of the virion contained within a viral envelope.

8 Claims, 14 Drawing Sheets

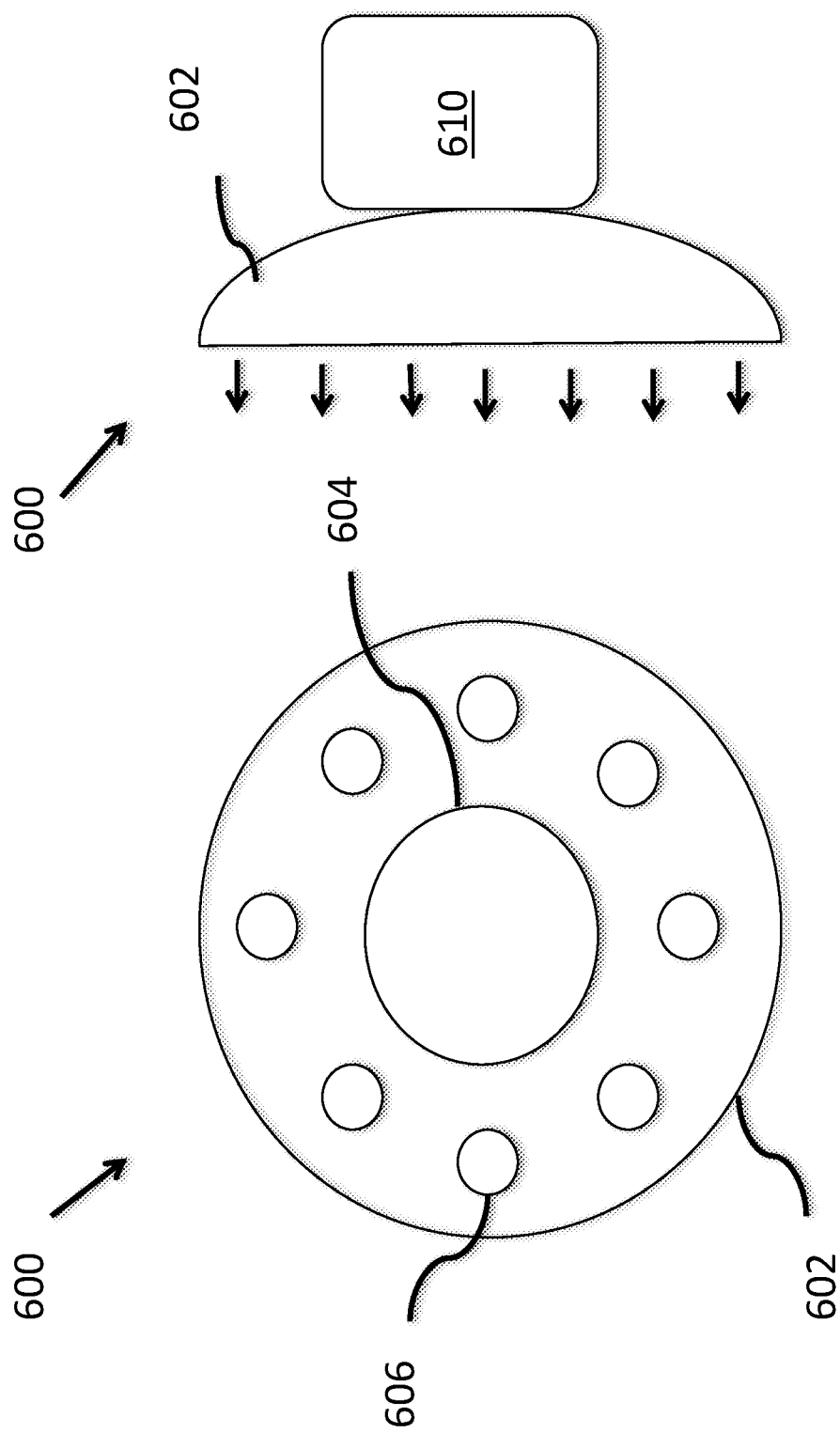

FREQUENCY SELECTIVE VIRAL INACTIVATION THROUGH BOND BREAKING

CROSS-REFERENCE TO RELATED APPLICATION(S)

The present application claims priority to U.S. Provisional Patent Application No. 63/050,458 filed on Jul. 10, 2020, entitled "Frequency Selective Viral Inactivation through Bond Breaking" the entire disclosure of which is incorporated by reference herein.

BACKGROUND

Pandemics caused by coronaviruses, such as SARS-CoV-2, can have devastating effects on health and the economy. SARS-CoV-2 is the coronavirus that causes the disease, COVID-19. A coronavirus is an enveloped virus, such as SARS-CoV-2, that contains single-stranded ribonucleic acid (RNA). A surrounding protein coat, referred to as a capsid, protects the RNA. The viral envelope, having a lipid bilayer membrane, serves as another protective coat, containing proteins and phospholipids, and it encloses the capsid. Spike proteins, which are crown-like in appearance, lie within the envelope. Envelope protein and membrane protein provide structural integrity to the virus (referenced as a "virion" outside of a host cell), and are interspersed among spike protein in the lipid bilayer membrane. The genome (the genetic material) of the virus is contained in its RNA in the form of a sequence of nucleotides that encode the synthesis of gene product (e.g., RNA or a protein). The spike protein in a coronavirus serves as the attachment tool for the virus to bind to a host cell. A coronavirus binds via its spike protein to a receptor, such as angiotensin-converting enzyme 2 (ACE2), an enzyme that is attached to the cell membranes of cells typically found in the respiratory track. ACE2 enzymes are organic molecules of catalytic proteins. The virus' hijacks a host cell's protein-making machinery causing the host cell to replicate viral proteins and RNA, which may assemble into copies of the virus. Hundreds of virions may result which may result in the virus infecting other host cells. RNA replication, like DNA replication has error correction (also known as proof reading) capability in replicating a genome sequence. However, RNA replication generally does not extend to the entire genome. For instance, coronavirus lacks post-replicative repair in certain regions of its genome. Consequently, mutations of RNA viruses, such as coronaviruses, may frequently occur, particularly as it relates to the genetic coding of the spike protein and accessory proteins. These mutations may possibly even allow a coronavirus to bind to new receptors. As the genome sequence of coronaviruses is relatively long (the longest of any other known RNA virus), replication of an RNA strand may be more prone to error than other viruses (the longer the sequence, the more chances for replication error/mutation).

Because of the damaging health, social, and economic effects of viruses, means and methods for inactivating them by attacking one or more of the previously mentioned viral components have long been sought after. For example, the lipid bilayer membrane is susceptible to degradation from detergents, soap and water, various disinfectants, etc. Further, heat and humidity may also damage this membrane. Once the viral envelope is damaged, this may lead to a virion losing its ability to bind to functional receptors.

Another approach to viral inactivation is to attack the RNA strand. The RNA strand in a virion is particularly subject to damage from ultraviolet (UV) radiation/light. It has been found that UV-C radiation is most effective for inactivation of viruses. However, the UV-C range of radiation can potentially cause negative effects from exposure, such as sunburn, skin cancer and eye cataracts.

Killing viruses/virions has become a top priority with the advent of the SARS-CoV-2 virus. Disinfecting surfaces and air is a concern that extends to every community for every room around the world, in order to inactivate known virions/viruses and virions/viruses yet to come, especially in present and/or future pandemics.

Particularly, given the potential flexibility of possible mutations relating to the spike protein of a SARS-CoV-2 virion, it is desirable to have a method and/or apparatus for destroying the structural integrity of the viral envelope. Further, a need exists to provide a reliable method to inactivate virions/viruses by both destroying the viral envelope as well as by modifying and damaging the RNA within the viral envelope. Successfully addressing these needs may lead to a solution to retard the spread of COVID-19.

BRIEF DESCRIPTION OF THE DRAWINGS

For a more complete understanding of the present disclosure, the objects and advantages thereof, reference is now made to the ensuing descriptions taken in connection with the accompanying drawings briefly described as follows.

FIG. 4b illustrates a continuation of the operational flow shown in FIG. 4a.

FIG. 6a illustrates a plan view of a cleaning apparatus which may include combinations of sources of radiation for room light including UV light/radiation, and IR light/radiation.

FIG. 6b illustrates a side view of the cleaning apparatus shown in FIG. 6a.

FIG. 8b illustrates a perspective view of a UV light source as shown in FIG. 8a.

Applicable reference numbers have been carried forward.

DETAILED DESCRIPTION

Figure 1A:
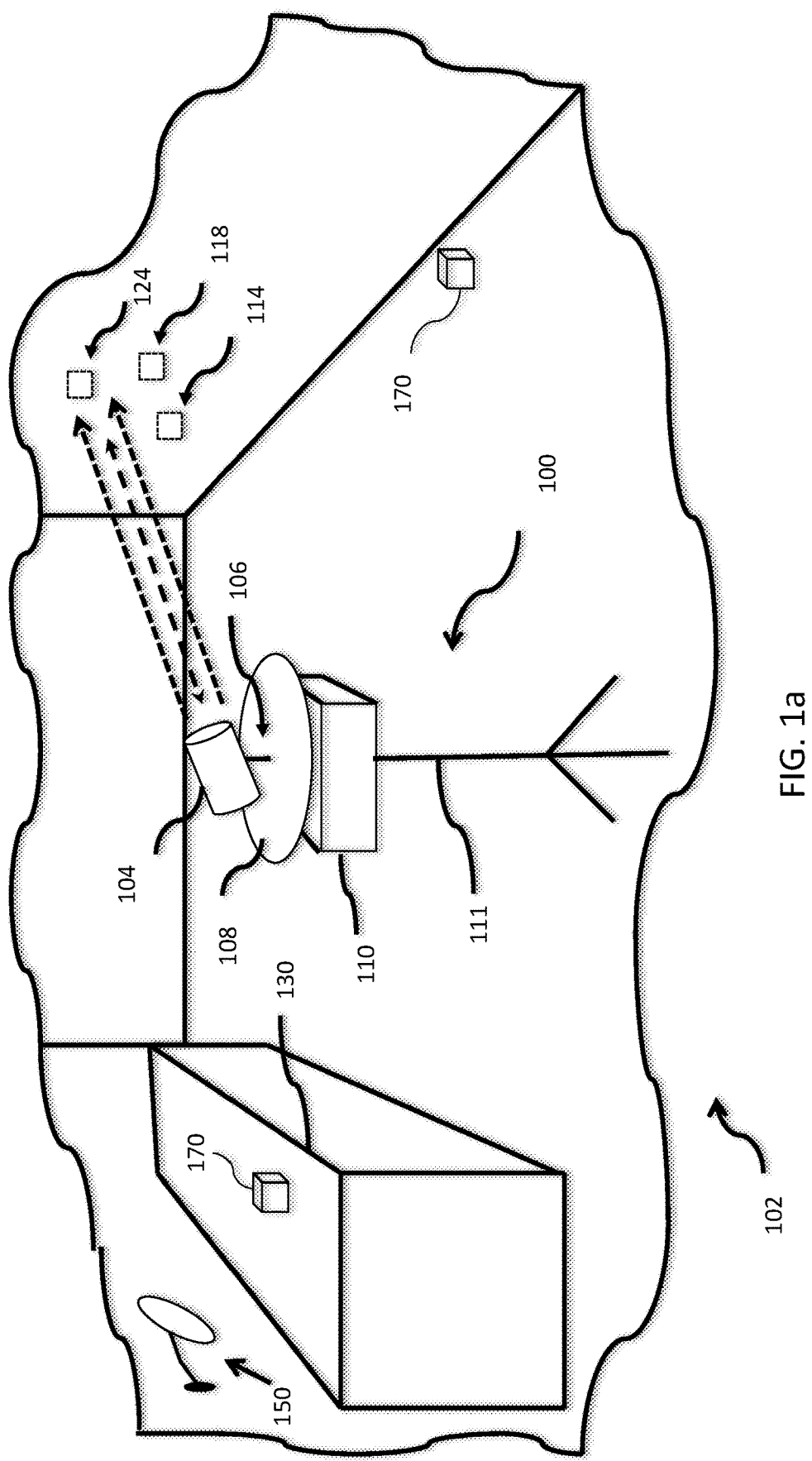
FIG. 1a illustrates a cut-away perspective view of a cleaning apparatus in an enclosure.

FIG. 1a illustrates a cut-away perspective view of cleaning apparatus 100 in enclosure 102. Cleaning apparatus 100 may provide both infrared and ultraviolet light radiation dispersal and monitoring to an enclosure 102, whether it be a box, a surface, an item, or a room such as an office, a kitchen, a laboratory, a hospital space, etc. Radiation source housing 104 may contain, among other things, a source of UV light (not shown), a source of infrared light (not shown), a temperature sensing transducer (not shown), a camera, and an optional lens system (not shown) for focusing UV and/or infrared (IR) light at a target. Radiation source housing 104 may rest on mounting stem 106 which is attached, in one example, to turntable 108. Control unit 110 may contain an electro-mechanical turning mechanism (not shown) for positioning radiation source housing 104. In addition or alternatively, other mechanisms such as micro-electromechanical systems (EMs) technology may be employed to cause the adjustment of the direction and intensity of the radiation. Control unit 110 may be mounted on stand 111.

Alternatively, the various light sources, transducers, and lens systems described herein may be independently mounted to turntable 108 and each may be positioned independently of one another via an associated positioning system. Alternatively, in some examples, housing 104 may include some but not all of the aforementioned light sources, transducers and other systems with the remaining items grouped in a separate housing or independently mounted to turntable 108 and inclusive of a positioning system/apparatus. Also, multiples of one or more of the aforementioned light sources, transducers, and/or other systems, as desired, may be implemented in the previously mentioned apparatus/system(s).

In operation, cleaning apparatus 100 cleans enclosure or surface 102 by irradiating surfaces in enclosure or surface 102 with UV and/or IR radiation as defined by the frequency of light provided by the UV and IR light sources within radiation source housing 104. The UV light is contemplated as being in the UV-A, UV-B and UV-C spectra. The UV light sources discussed herein in regard to the drawing figures and claims may produce light of a discrete nature, such as that produced by a laser, or of a continuous nature, such as that produced by known UV bulb sources. Thus, the source of UV light and the source of IR light in radiation source housing 104 may be, for example, one or more lasers. A surface within a defined perimeter (e.g., a square inch) to be irradiated with UV light and IR light from radiation source housing 104. The UV light and IR light may be emitted, simultaneously on a target or, alternatively, one may follow the other. Turntable 108 may be actuated by an electro-mechanical turning mechanism (not shown) to rotate radiation source housing 104, systematically, so as to be able to irradiate a surface at which it is directed. The UV radiation is intended to degrade the DNA of a DNA virus or the RNA of a RNA virus (like SARS-CoV-2). Especially given the error correction capability of DNA and RNA viruses, should the UV radiation not be sufficient to effectively degrade the RNA or DNA (both of which define "genetic material") to the point of inactivation, the IR irradiation is intended to destroy the viral membrane of an enveloped virus/virion like SARS-CoV-2. The IR radiation is intended to heat the surface to the point where a viral membrane of a virion on the surface would be damaged or substantially degraded. Empirical data concerning one or more viruses may be used as a reference to determine the recommended duration of application at a power/intensity and frequency that is best able to destroy or degrade a particular viral envelope. It may be desired that only a particular surface in a room need be cleansed for purposes of time economy. For instance, radiation source housing 104 may be directed to be swept over a certain area, such as counter 130, to cause IR and/or UV irradiation, only, of counter 130, as opposed to a more substantial portion or all of the entire room (enclosure 102). One or more reflectors such as reflector 150, may be used to reflect IR and UV radiation onto surfaces which may be obscured from receiving irradiation directly incident from the IR and UV sources. One or more sensors (sensor 170) may be placed within enclosure 102. Sensor 170 may be used to send various readings to cleaning apparatus 100, which may include one or more processors (not shown) or microcontrollers (not shown). The readings may include information about various parameters (e.g., heat intensity, direction of radiation, duration of radiation, etc.) and they may be used by cleaning apparatus 100 to make adjustments, accordingly, to IR/UV radiation intensity, direction, duration, etc., based on the sensor readings.

Figure 1B:
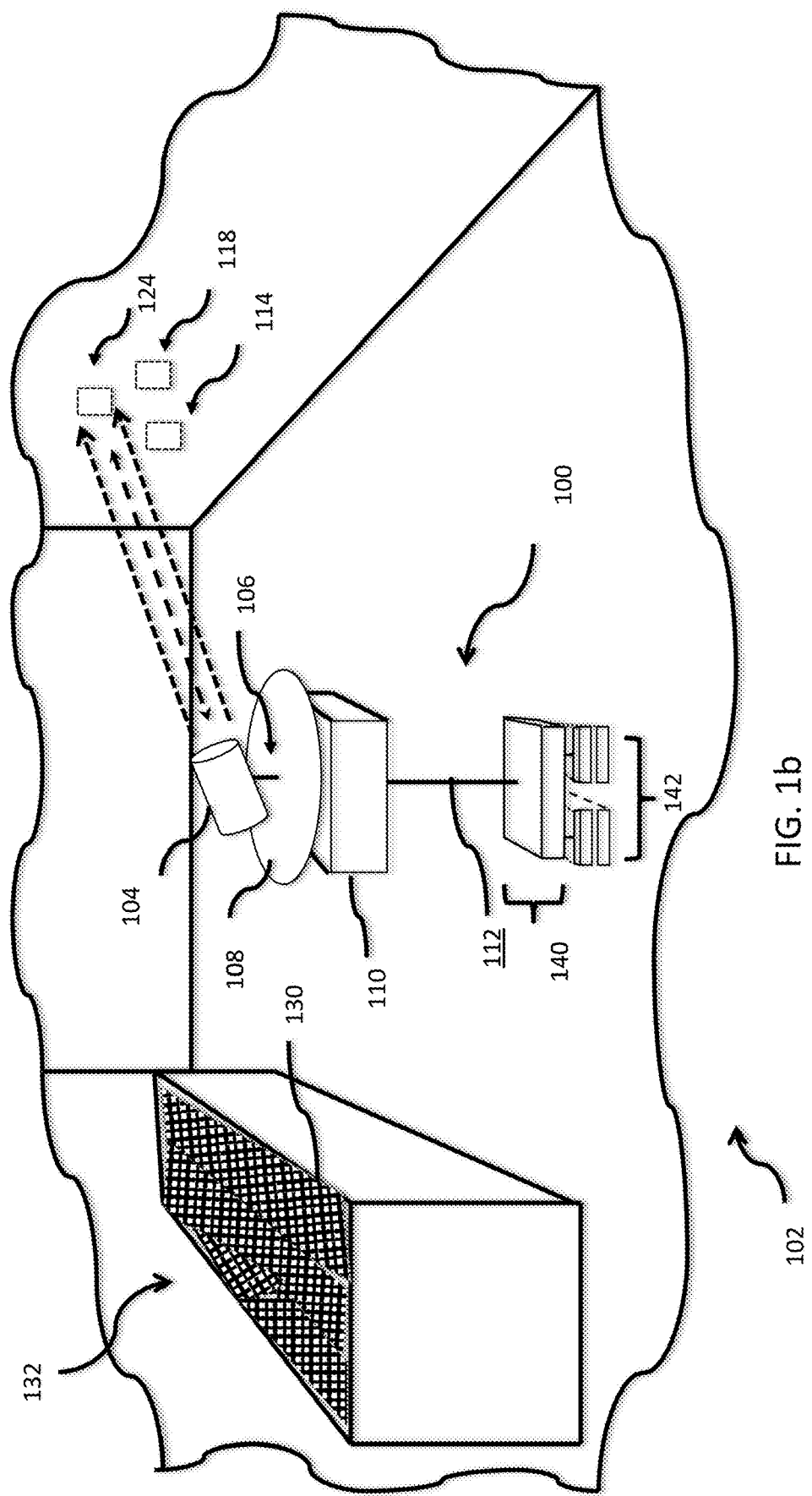
FIG. 1b illustrates an example of a cleaning apparatus having a control unit connected via a stem to a vehicle.

FIG. 1b illustrates an example of cleaning apparatus 100 having control unit 110 connected via stem 112 to vehicle 140. Vehicle 140 may be propelled using a pair of continuous tracks 142 or wheels (not shown). In other examples, vehicle 140 may be an unmanned aerial vehicle (UAV). Representative targets (114, 118 and 124) for irradiation are shown in dotted line outline. The one or more processors in control unit 110 are programmed to cause the one or more stepping motors within control unit 110 to position radiation source housing 104 so that radiation source housing 104 may systematically irradiate every target shown on a landscape map, further described below, which illustrates an area that has been selected for cleansing/disinfection. In some examples, the irradiation of targets may occur in connection with some overlap beyond the border with another target, so as to ensure complete irradiation coverage. Vehicle 140 may be controlled by one or more processors within control unit 110 to further position cleaning apparatus 100 so as to extend the range of radiation from radiation source housing 104 to reach areas which might otherwise be shielded from radiation by radiation source housing 104 had cleaning apparatus 100 been limited to only one stationary position.

With reference to FIGS. 1a and 1b, in operation, cleaning apparatus 100 may clean enclosure 102 in connection with using UV light and IR light to irradiate surfaces in a room with UV and/or IR radiation as defined by the frequency of light provided by the UV and IR light sources within radiation source housing 104. The one or more processors may be programmed to cause a photographic image of enclosure 102 to be taken and analyzed so as to produce a landscape map (a map of the surfaces from either the perspective of the cleaning apparatus 100 or a predetermined fixed reference point or points of enclosure 102, thereby avoiding the need to recreate landscape maps when apparatus 100 is used multiple times in regard to the same enclosure 102 of the surfaces to be irradiated within enclosure 102. The one or more processors may be programmed, in one example, to cause the landscape map to be parsed into parallelograms (e.g., squares, rectangles, etc.) defining contiguous sections on surfaces within enclosure 102, serving as/translating into targets, for irradiating with IR and/or UV radiation. Especially given the error correction capability of DNA and RNA viruses, should the UV radiation not be sufficient to effectively degrade the RNA or DNA to the point of inactivation, the IR irradiation is intended to destroy the viral membrane of an envelope virus/virion like SARS-CoV-2. As the IR radiation is intended to heat the surface of a target (e.g. a square inch area on a surface) to the point where a viral membrane of a virion on the surface would be destroyed or substantially degraded, a thermal radiation detector included within control unit 110, may be used to assess whether a targeted surface as defined by each target, has been sufficiently heated. Empirical data concerning one or more viruses may be used as a reference to determine the duration of application at a power intensity and frequency that is best able to destroy or degrade a particular viral envelope. Programming may be selected by a user, to program the one or more processor to cause the application, by radiation source housing 104, of IR and/or UV radiation, to a targeted surface, that is selective to a particular virus/ virion. Further, it may be desired that only a particular surface in a room need be cleansed for purposes of time economy. For instance, the one or more processors in radiation source housing 104 may be programmed to cause IR and/or UV irradiation of frequently contacted or highly likely to be contacted surfaces, such as counter 130, door-knobs, cabinet doors, or the like, only, as opposed to a more substantial portion or all of the entire room (enclosure 102). A series of contiguous targets 132 (each target shown as a small rectangle, by way of example only) on counter 130, may be defined according to a series of contiguous perimeters on a landscape map (not shown) according to programming of the one or more processors within control unit 110. The programming may allow a user to, for instance, from a menu displayed on a user interface (on control unit 110 or on a display of a device linked to control unit 110), shade, on the display, portions of a photographic image using a computer mouse, cursor, etc., for application of the noted IR and/or UV irradiation upon a corresponding surface. It is contemplated that programs and/or programming instructions to the one or more processors of control unit 110 may be available, as well, to a user using a computing device to control the operation of cleaning apparatus 100 through the one or more processors in control unit 110. Once every selected surface, has been irradiated (referred to herein as "painted"), cleaning/disinfecting of viruses from those surfaces may be accomplished.

Figure 2:
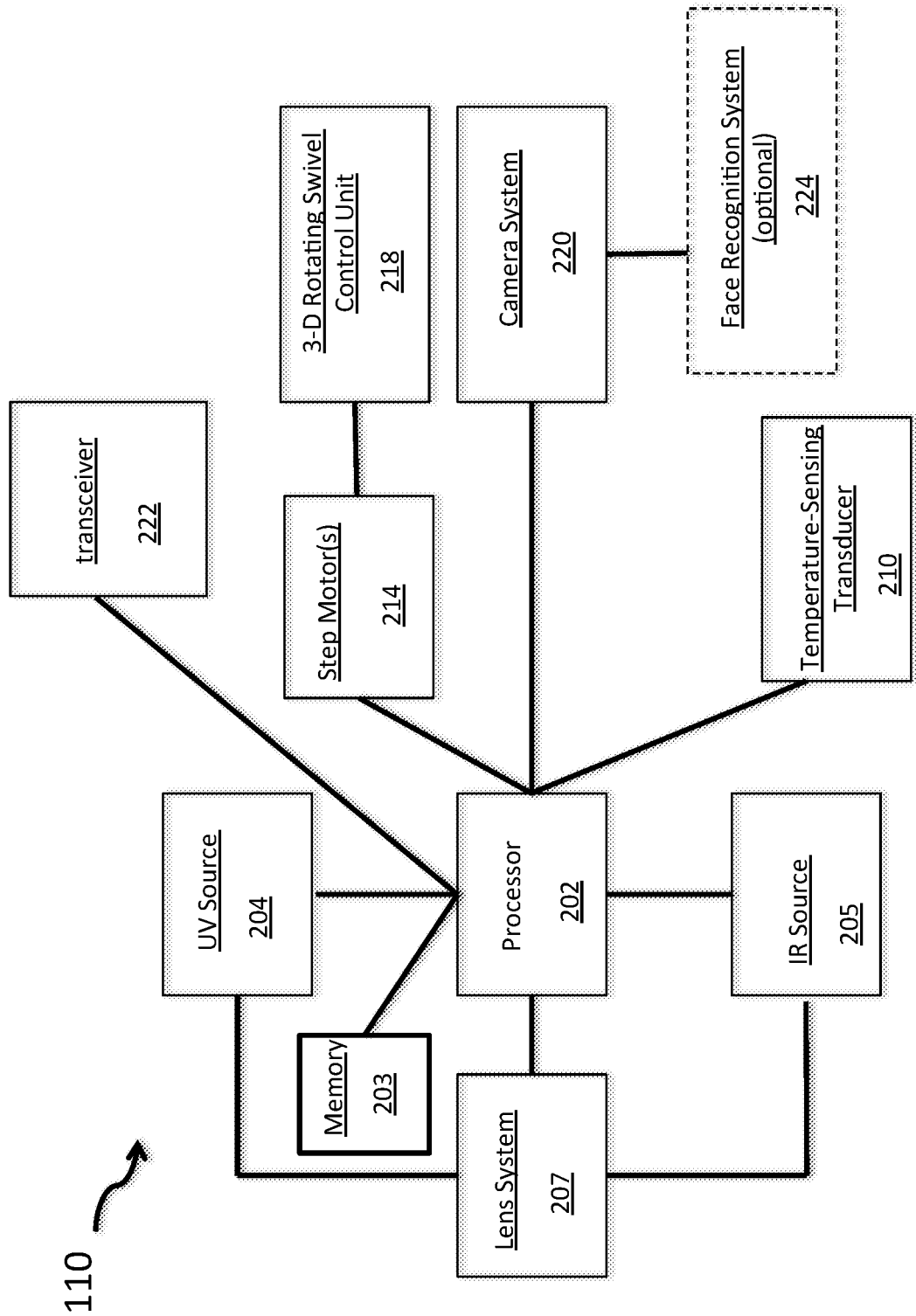
FIG. 2 illustrates a block diagram of a control unit.

FIG. 2 illustrates a block diagram of control unit 110. Processor 202 may reference one of more processors for controlling, according to programming, various aspects of cleaning apparatus 100 (FIG. 1). Processor 202 may access programming instructions from or provide and access data to/from memory 203. Processor 202 may also be coupled to UV source 204 and IR source 205 to control the intensity and frequency thereof. Lens system 207 may be controlled by processor 202 to help further focus light from UV source 204 and/or IR source, especially when those sources are not laser sources. Where lasers are used as light sources, it may be desirable to use them in conjunction with appropriate lenses or diffusers, which may be included within lens system 207, in order to enlarge the effective surface area covered by an attendant laser beam. Lasers tend to produce a small beam area (on the order of 0.5 square millimeters, for example) in comparison with other sources of light. Covering a large surface using only a small beam may account for a level of complexity which may be avoided by spreading the beam. Less positioning precision may be required in connection with spreading the beam than otherwise and surface areas may be covered more quickly. Doing so may, depending upon the initial power of the laser sources, require a step-up in laser intensity to ensure that an area can be disinfected within a desired time frame.

Temperature-sensor 210 (which may be a laser light infrared thermometer) may be used by the processor 202 to determine the temperature of a surface both before and after application of IR radiation, pursuant to attaining a predetermined temperature or difference in temperature (delta) after application of the IR irradiation. Alternatively, temperature-sensor 210 may be used to check the temperature of a surface after irradiation to ascertain whether a targeted surface temperature has been attained. Step motor(s) 214, (of which there may be, for instance, one to three step motors for controlling pitch, yaw and roll angles of radiation source housing 104 (FIG. 1)) is connected to and controlled by processor 202. Step motor(s) 214 may direct three-dimensional rotating swivel control unit 218 which may control the position of radiation source housing 104 (FIG. 1). Processor 202 may be coupled to camera system 220 which may include a camera. Alternatively, camera system 220 may provide an interface for a mobile device (smart phone, tablet, computer, etc.) through which the camera on the mobile device may be used to photograph enclosure 102 and render a photo for use by processor 202 in connection with a program running thereon for determining the landscape map for irradiating target surfaces. Augmented reality may additionally be used to produce the landscape map from an image. Processor 202 may receive programming or instructions through transceiver 222. In lieu of a single unit, such as transceiver 222 for reception and transmission of information, the functions provided by transceiver 222 may be implemented as a separate transmitter and a separate receiver. In one example, face recognition system 224 may be optionally used, as controlled by processor 202, to detect individuals in the room, undergoing cleaning, according to the foregoing. Alternatively or in addition thereto, face recognition system 224 may represent or may include a camera system or motion sensor/system for detection of individuals (or, for example, laboratory animals, etc.) needing protection from the irradiation to be provided to enclosure 102. The cleaning operation may be halted as a consequence of detection of a living entity in the room. This aspect can be extremely beneficial, especially in connection with irradiation using the UV-C spectrum.

Figure 3:
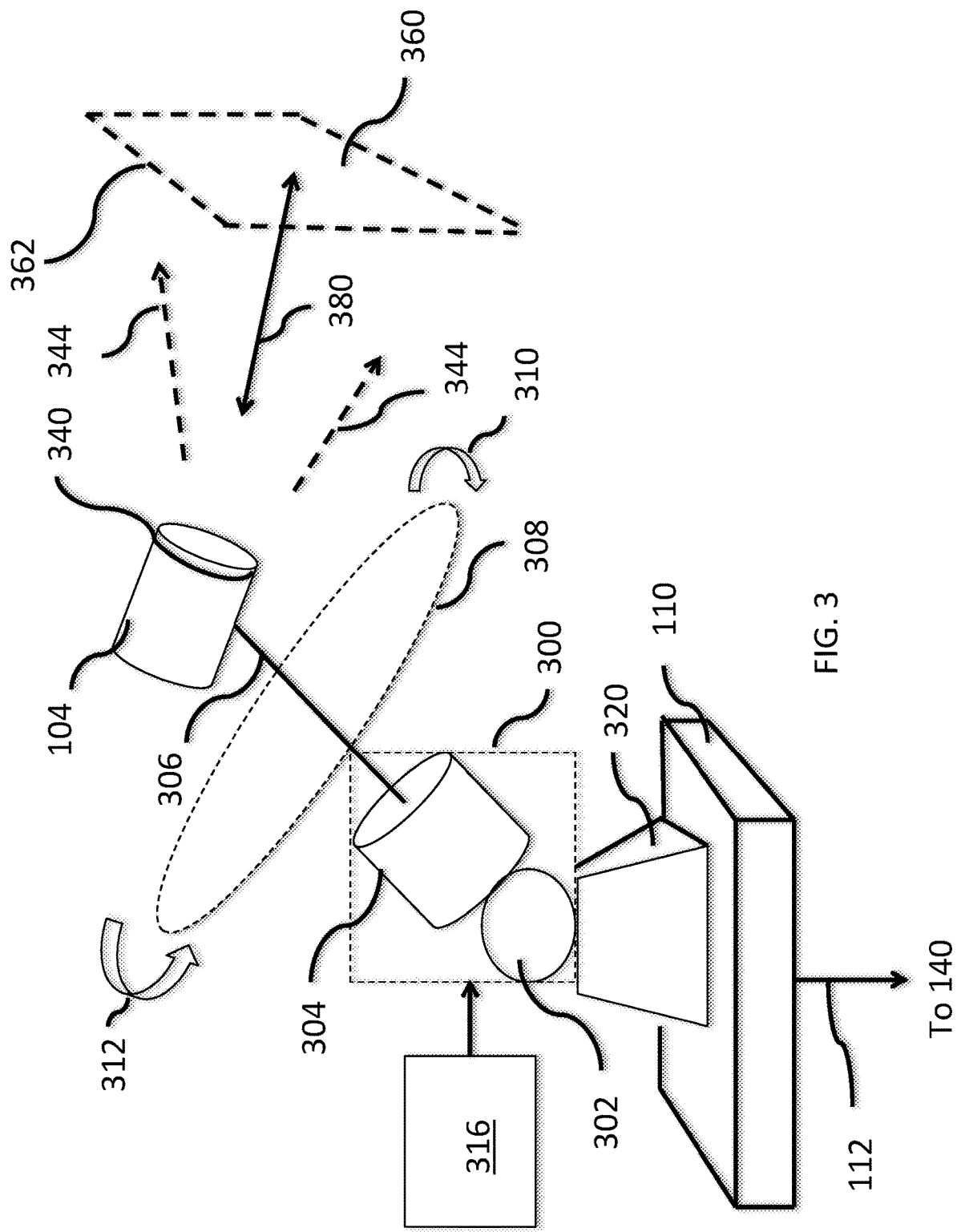
FIG. 3 illustrates a perspective view, having a schematic component, of a portion of a cleaning apparatus.

FIG. 3 illustrates a perspective view, having a schematic component, of a portion of the cleaning apparatus as disclosed herein. Positioning apparatus 300 may include apparatus for moving radiation source housing 104 (FIG. 1). In one example, positioning apparatus 300 may include gimbal 302 connected to base 304 on which telescoping stem 306 is mounted. Telescoping stem 306, connected to radiation source housing 104, may adjustably extend back and forth to move radiation source housing toward or away from base 304. Telescoping stem 306 may also be rotated around circular path 308 in a clockwise manner (310) and/or in a counterclockwise manner (312). One or more step motors 316 may control positioning apparatus 300, specifically, gimbal 302. Alternatively, telescoping stem may rotate around its axis. Positioning apparatus 300 may physically rest on support 320 which may lie on control unit 110. Lens system 340, which may lie at the end of radiation source housing 104, may include one or more lens for focusing light 344 at target surface 360 defined by a parallelogram 362 (shown as a square or rectangle). Other target shapes (circles, parabolas, etc.) are contemplated and can be used with the cleaning apparatus as described herein. Double arrow 380 denotes the dispatch and reflection of an infrared signal from temperature-sensor 210 (FIG. 2). Vehicle 140 (FIG. 1*b*) may help position positioning apparatus 300, gimbal 302 and telescoping stem 306 to ensure that radiation source housing 104 can irradiate targets.

Figure 4A:
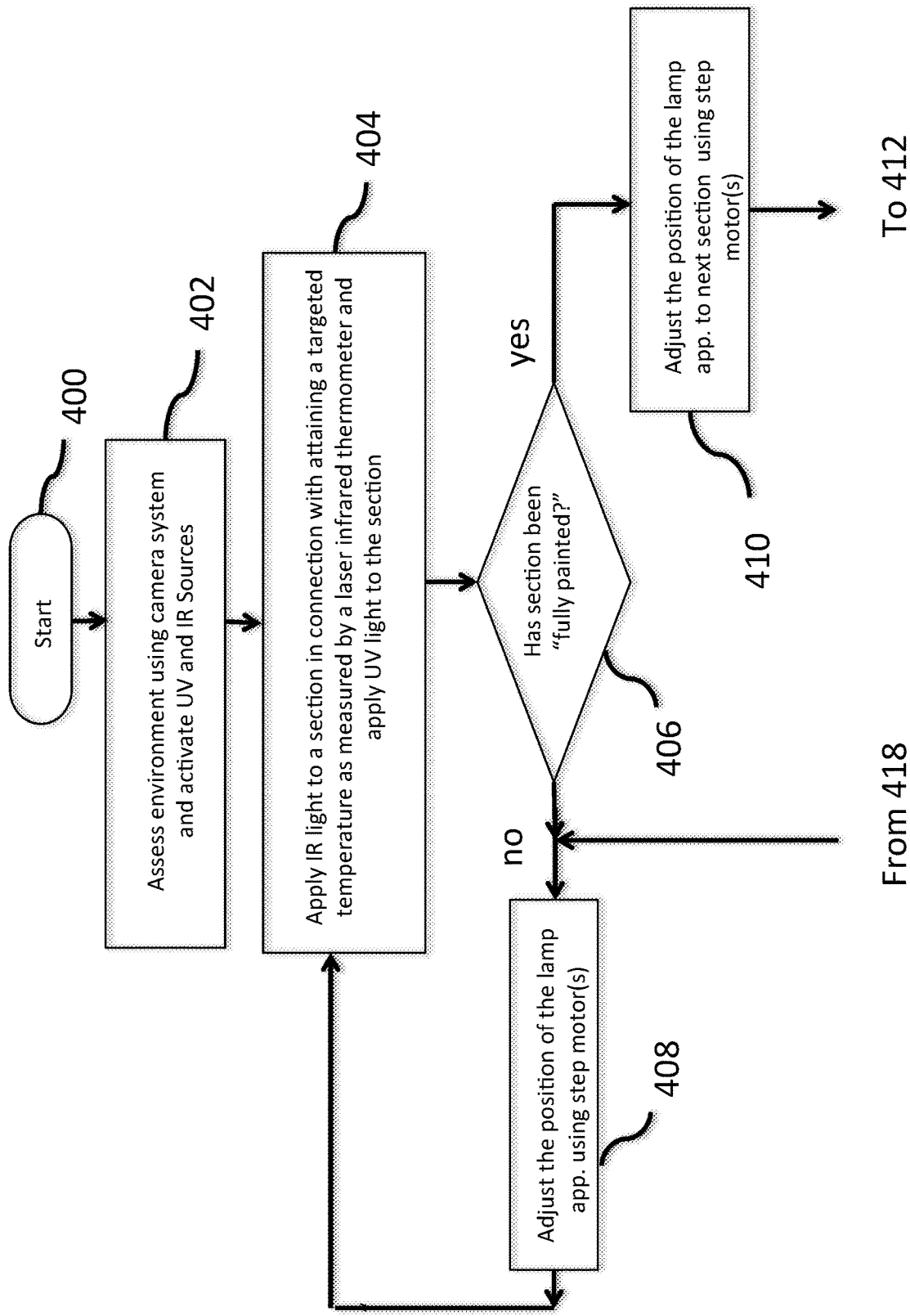
FIG. 4a is a flow chart showing an exemplary operational flow.
Figure 4B:
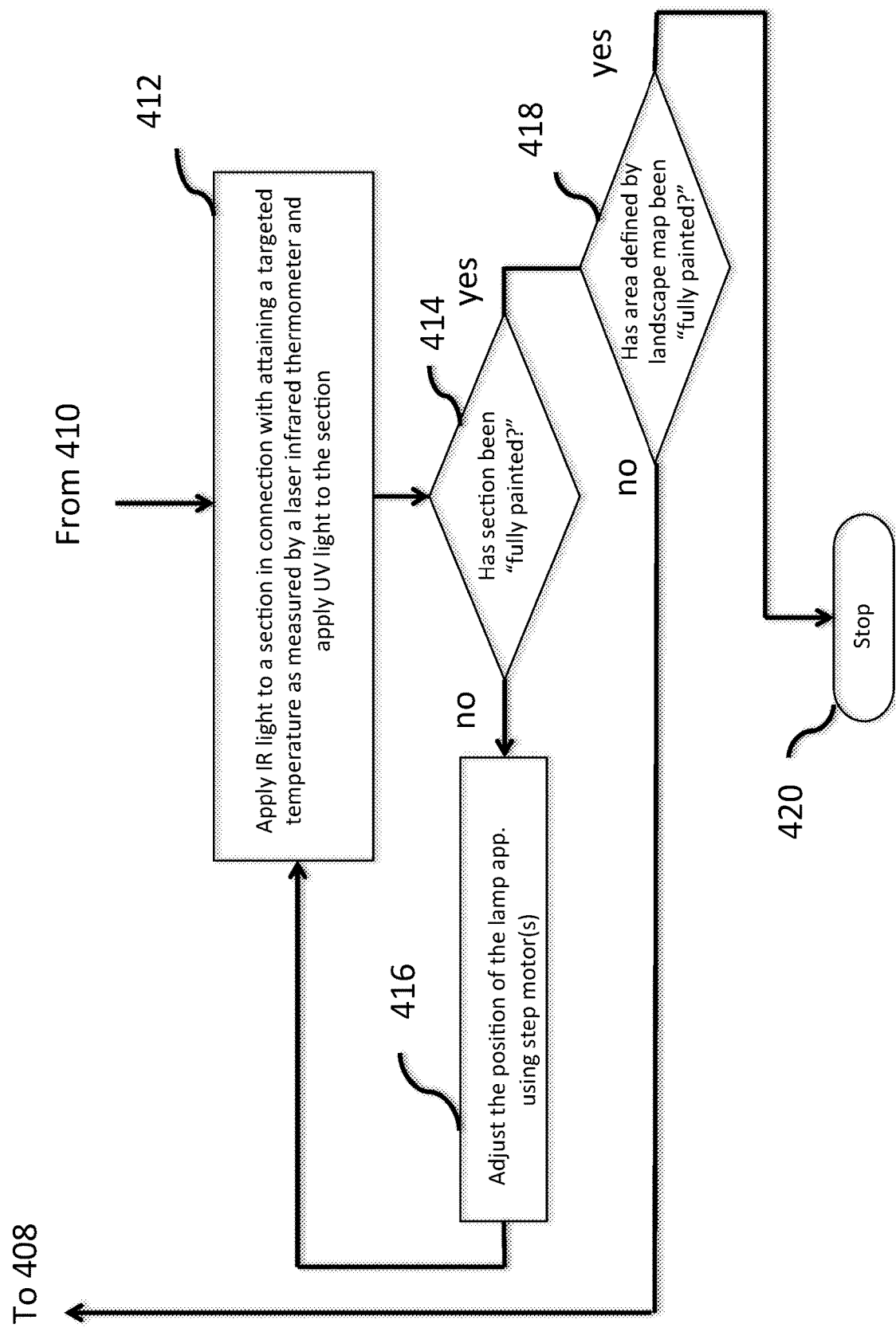

FIG. 4*a* is a flow chart showing an exemplary operational flow according to the foregoing. FIG. 4*b* illustrates a continuation of the operation flow shown in FIG. 4*a*. With reference to FIGS. 4*a* and 4*b*, the flow starts at step 400. The environment is assessed at step 402 in conjunction with a camera system and UV and IR light sources are activated. Step 402 may include taking a photo of the enclosure to be cleaned/disinfected and the rendering of a landscape map pursuant to cleansing/disinfecting of an area. At step 404, IR light is applied to a section of a surface in connection with attaining a targeted temperature as measured by a laser infrared thermometer. Further, UV light is applied to the section. "Section" as used herein, may refer to, for instance, a square inch section selected for irradiation according to the landscape map. At decision step 406, a determination is made as to whether irradiation has taken place over the entire surface of a section defined by a landscape map. Irradiating the entire surface is referred to herein as being "fully painted." If the section has not been fully painted, then the position of a light source (such as radiation source housing 104 (FIG. 1)) is adjusted at step 408, to permit irradiation of the remainder of the section, in connection with using one or more step motors. The operational loop continues, among steps 404, 406 and 408, until the section has been "fully painted." Thereafter, once the section has been "fully painted," at step 410, the light source is positioned to the next section, as defined by the landscape map, using one or more step motors. The operational flow from step 410 continues to step 412 in FIG. 4*b*.

As shown in FIG. 4*b*, at step 412, IR light is applied to another section of a surface (to which the lamp apparatus is positioned at step 410) in connection with attaining a targeted temperature as measured by a laser infrared thermometer. Further, UV light is applied to this section. At decision step 414, a determination is made as to whether this section has been "fully painted." If the section has not been fully painted, then at step 416, the position of the lamp apparatus is adjusted to permit irradiation of the remainder to the section. The operational loop continues among steps 412, 414 and 416 until the section has been "fully painted." Once the section has been "fully painted," at step 418, a decision is made as to whether the area defined by the landscape map for cleansing has been "fully painted." If the area has been "fully painted," then the operational flow stops at step 420. If not, the operational flow continues from step 418 in FIG. 4*b* to step 408 of FIG. 4*a*.

Figure 5A:
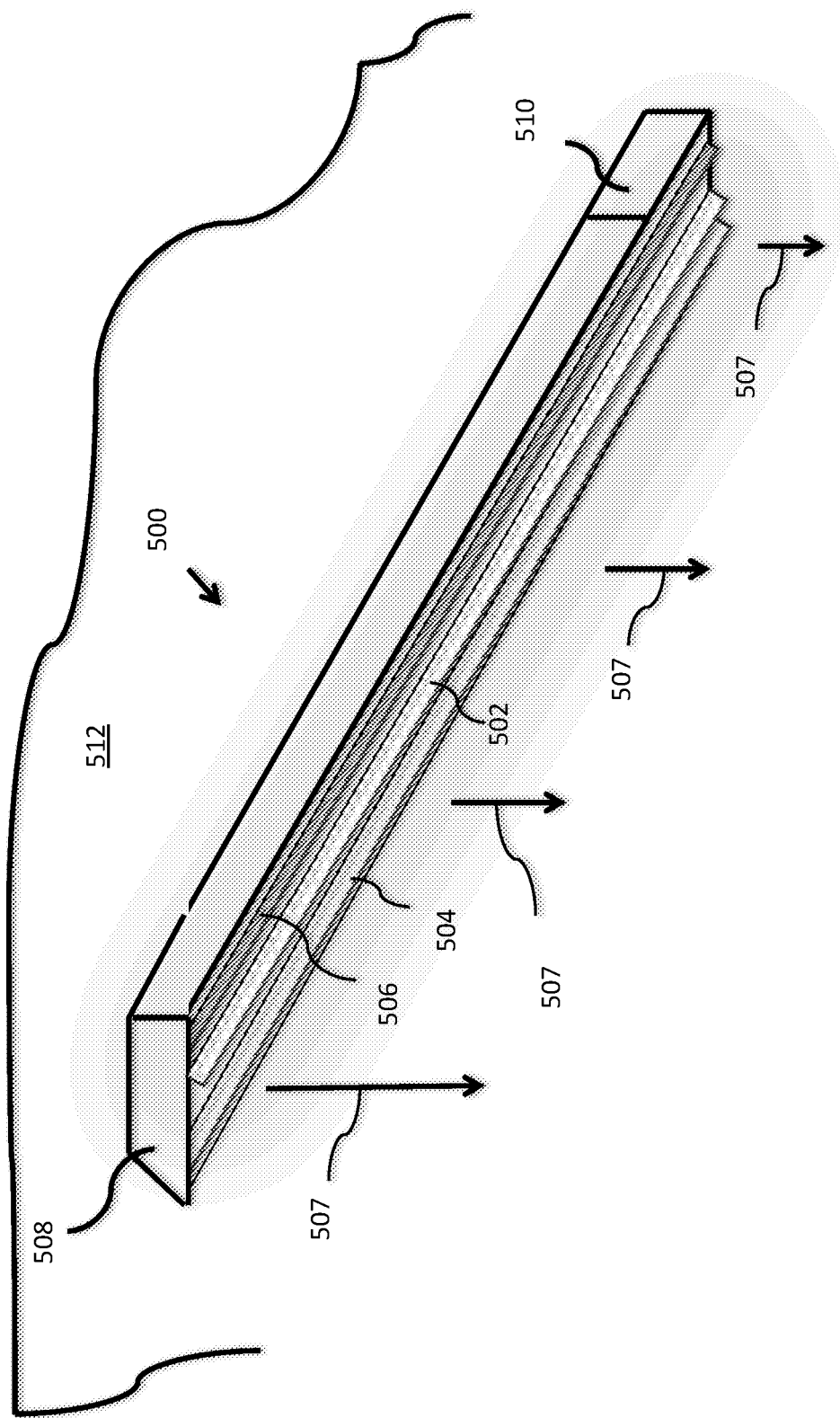
FIG. 5a illustrates a perspective view of a light apparatus which may include combinations of sources of radiation for room light, UV light/radiation, and IR light/radiation.

FIG. 5*a* illustrates a perspective view of light apparatus 500 which may include combinations of sources of radiation for UV light/radiation and IR light/radiation. Light apparatus 500 may be configured to be repositionable and thus may be used in multiple locations within a single enclosure. Additionally, if desired, light apparatus 500 may include a source of visible spectrum room light such as, by way of example, LEDs, fluorescent bulbs, or incandescent bulbs (one or more of which may be optional for inclusion). In the example shown for light apparatus 500 in FIG. 5*a*, light source 502, IR light source 504 and UV light source 506 are housed in light fixture 508. Control unit 510 may attach to fixture 508 and house control apparatus (not shown) for light apparatus 500. Control apparatus within control unit 510 may include communication equipment such as a receiver, transmitter or transceiver for receiving and transmitting information pertinent for control (via one or more processors (not shown), within or exterior to control unit 510) of light source 502, IR light source 504 and UV light source 506. Control unit 510 may also include one or more transformers for delivering power to the sources of radiation (502, 504, 506). Additionally, in some examples, control unit 510 may contain one or more band-pass filters which may pass certain frequencies of light and filter out others. Further, a camera system, an object recognition system, and/or a motion detection system may be coupled to a processor (not shown) within or exterior to control unit 510.

The sources of light/radiation 502, 504, 506 may be operated simultaneously or in various combinations of being turned on or turned off. Lenses (not shown) for further focusing light 507 may be placed over one or more of the sources of light/radiation (502, 504, 506), or, where the UV and/or IR light source contain a laser, such lenses may be dispersive in nature, such as a concave lens, so as to spread out the otherwise narrow laser beam to cover a larger surface area. Alternatively, in lieu of a lens, an appropriate frosted glass or other dispersive device may be used. Light fixture 508 may be attached to many different surfaces, such as ceiling 512. In some examples, sources of light/radiation (502, 504, 506) may include one or more filters such as band-pass filters.

Figure 5B:
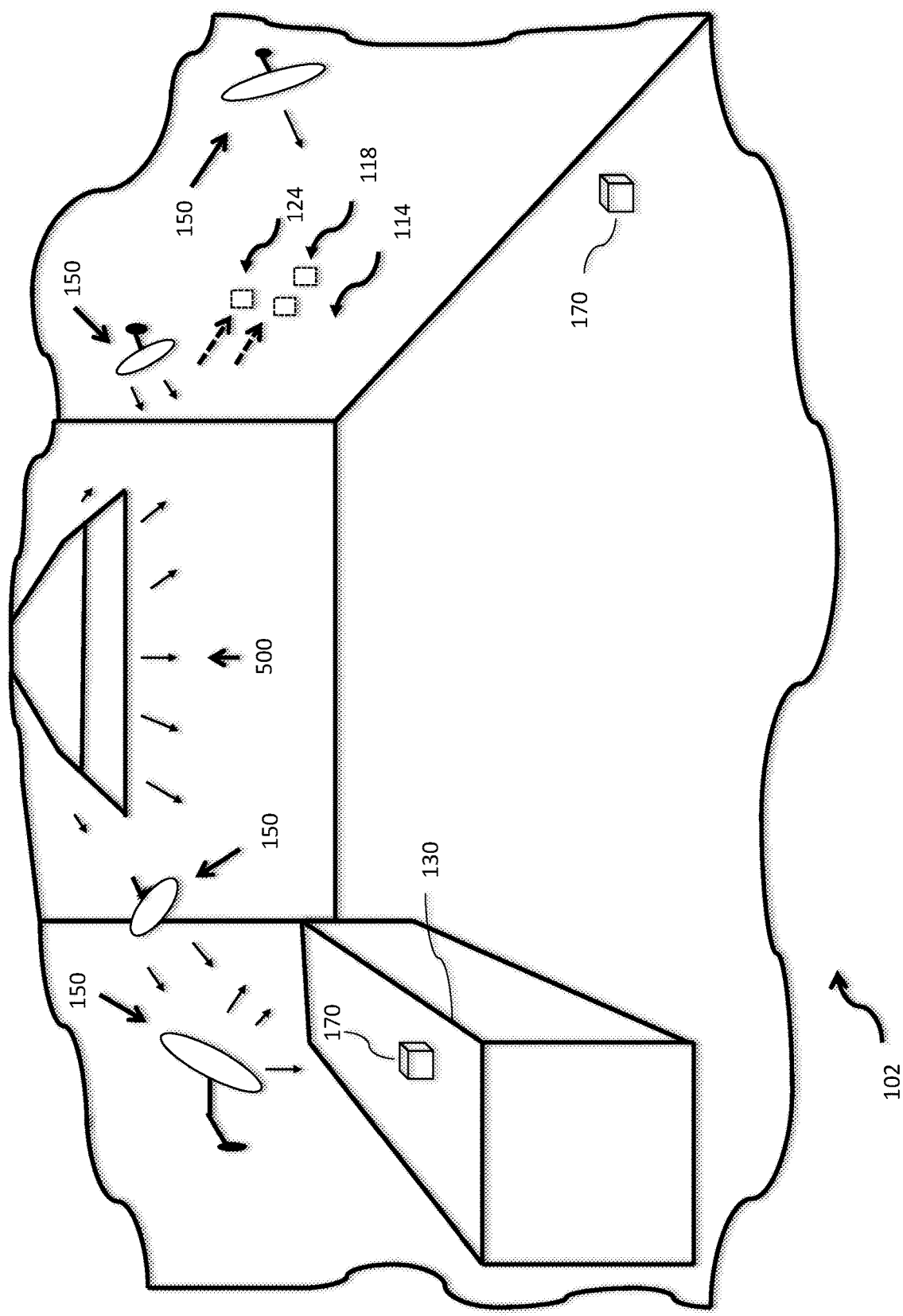
FIG. 5b illustrates a perspective view of a light apparatus suspended from a ceiling in an enclosure representing a room.

FIG. 5*b* illustrates a perspective view of mobile cleaning apparatus 500 suspended from a ceiling (not shown) in enclosure 102 representing a room. Radiation may emanate from light source 502, IR light source 504 and UV light source 506 (of FIG. 5*a*) onto surfaces with enclosure 102 and in the air in enclosure 102. One or more reflectors (such as reflector 150) may help irradiate surfaces which may be obscured from a direct path to a light/radiation source. Sensor 170 may be used to send various readings to cleaning apparatus 500, which may include one or more processors (not shown) or microcontrollers (not shown). The readings may include information about various parameters (e.g., heat intensity, direction of radiation, duration of radiation, etc.) and they may be used by cleaning apparatus 500 to make adjustments, accordingly, to IR/UV radiation intensity, direction, duration, etc., based on the sensor readings.

FIG. 6*a* illustrates a plan view of a cleaning apparatus 600 which may include combinations of sources of radiation for room light, UV light/radiation, and IR light/radiation. Cleaning apparatus 600 includes a curved-shaped fixture 602. Center radiation/light source 604 and surrounding radiation/light sources 606 (only one labeled) around center radiation/light source 604 represent one example of configuration in which room light, UV and IR sources of light/radiation may be arranged within curved-shaped fixture 602. For example, center radiation/light source 604 may represent one or more incandescent light sources, laser light sources (such as pulsed laser light sources), light emitting diode (LED) sources, liquid crystal display (LCD) diode sources or combinations thereof of which some may emit radiation in the UV (UV-A, UV-B and UV-C) and IR spectrums. Further, surrounding radiation/light sources 606 may represent one or more incandescent light sources, laser light sources (such as continuous and/or pulsed mode operating laser light sources), light emitting diode (LED) sources, liquid crystal display (LCD) diode sources or combinations thereof which include sources of IR and UV radiation. Cleaning apparatus 600 may be carried by hand or used in or mounted in a vehicle. Cleaning apparatus 600 may be used while powered in connection with a power source (not shown).

FIG. 6*b* illustrates a side view of the cleaning apparatus 600 shown in FIG. 6*a*. Control unit 110 as described above with respect to FIG. 3*a* is shown attached at the rear of curved-shaped fixture 602. However, control unit 610 may be located elsewhere or even remotely from curved-shaped fixture 602. Although curved-shaped fixtures have been shown and discussed in FIG. 6*a* and FIG. 6*b*, other shapes for fixture 602 have been contemplated (parabolic, spherical, rectangular, etc.).

Figure 7:
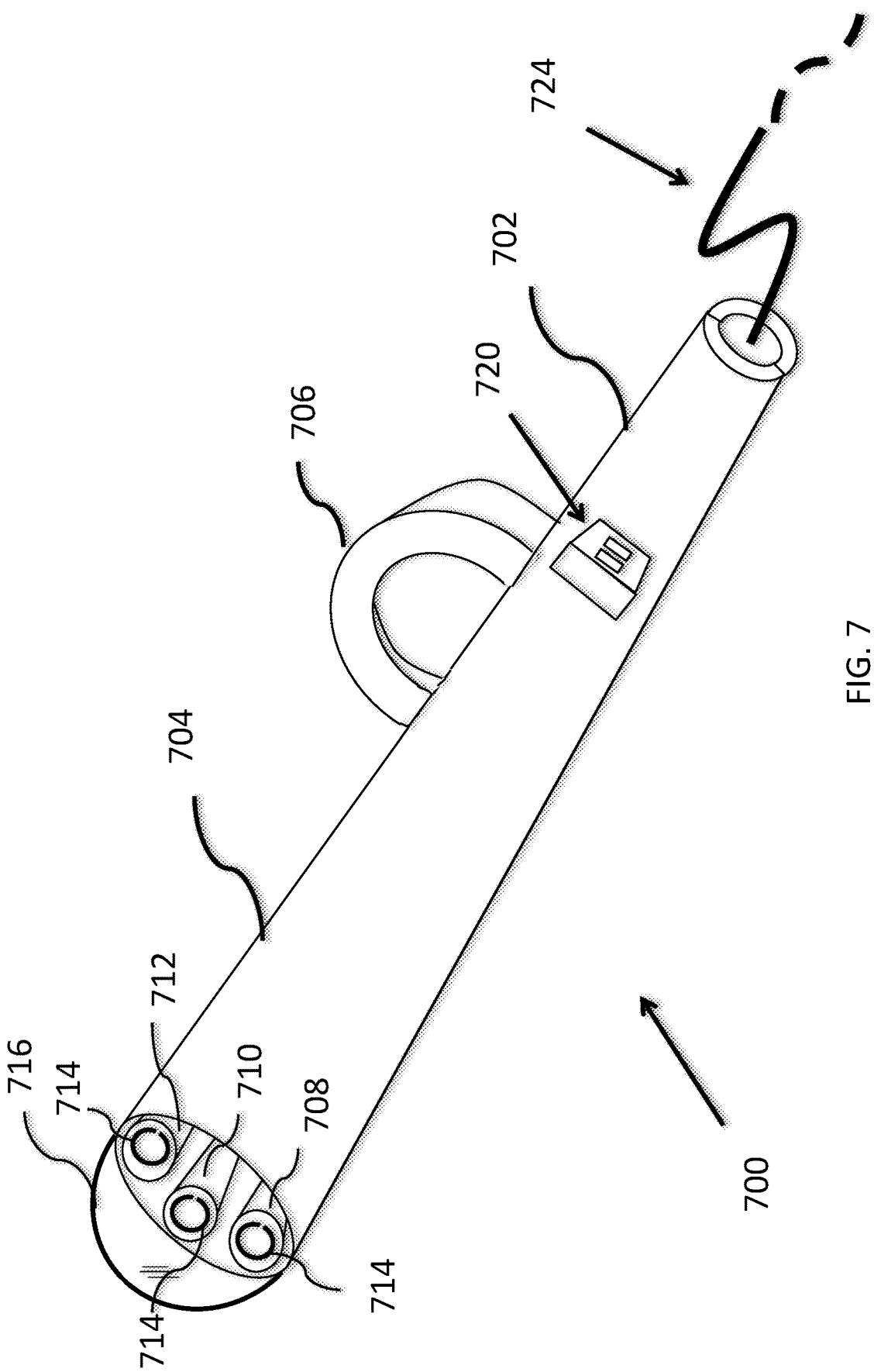
FIG. 7 illustrates a perspective view of a mobile wand device which may be used to sanitize areas on which virions may exist.

FIG. 7 illustrates a perspective view of a mobile wand 700 which may be used to sanitize areas on which virions may exist. Mobile wand device 700 may be handheld, for example, near stem 702. Additionally, mobile wand device 700 may include wand fixture 704 which may have a variety of cross-sectional shapes, such as cylindrical, square, etc. Wand fixture 704 may be fitted with one or more handle(s) 706. Radiation sources 708, 710 and 712 may be housed within wand fixture 704 and may be selected from one or more incandescent light sources, laser light sources (such as continuous and/or pulsed mode operating laser light sources), light emitting diode (LED) sources, liquid crystal display (LCD) diode sources or combinations thereof. Lens 714 may be present over each radiation source 708, 710 and 712, or over selected ones of radiation sources 708, 710 and 712. Radiation sources 708, 710 and 712 may include combinations of IR sources and UV sources. Lens 714 may further focus light emitted from a radiation source (708, 710 and 712), or, may serve to disperse or diffuse the light from one or more of radiation sources 708, 710 and 712, depending upon the nature of the light emitted by the particular radiation source so as to achieve broader coverage than would be provided by a laser or a focused light source. Protective housing 716, shown configured as a transparent dome in the example shown, may serve to protect mobile wand device 700 and radiations sources 708, 710 and 712. In one example, protective housing 716 may also serve as a light-focusing lens. In another example, protective housing 716 may serve to disperse UV light provided by a laser of a preselected wavelength. Because lasers commonly produce a narrow beam covering a small area, dispersing the beam may enable virus-inactivating coverage of a larger area and, for example, reduce the time necessary to disinfect a particular surface of interest. Examples of such a dispersive housing 716 are a concave lens or frosted glass. While protective housing 716 is illustrated as a dome-like structure in the FIG. 7, other shapes, such as the substantially flat covering of common flashlights, may also be utilized. In one example, transparent dome 716 may also serve as a light-focusing lens or diffusive element depending upon the activated radiation source. Wand control unit 720 is shown located on wand fixture 704 and it may house controls for mobile wand device 700. It is also contemplated that mobile wand device 700 house one or more power transformers for powering radiation sources 708, 710 and 712 selected from one or more incandescent light sources, laser light sources (such as continuous and/or pulsed mode operating laser light sources), light emitting diode (LED) sources, liquid crystal display (LCD) diode sources and combinations thereof. Electrical cord 724, which may be coupled to wand control unit 720, may supply electricity to power mobile wand device 700. With sufficient battery power, cord 724 may be obviated.

Mobile wand 700 is also contemplated as being for use in a vehicle, particularly a rideshare vehicle. Handle(s) 706 may be used to facilitate hanging or mounting mobile wand 700 inside of the vehicle (not shown). Alternatively, a holder (not shown) may be provided for mobile wand 700 within the vehicle. In some examples, wand control unit 720 may contain a wireless controller (Bluetooth™, Bluetooth™ Low Energy (LE), WiFi, etc.) for controlling mobile wand 700 using a mobile device (smart phone, tablet, etc.). In connection with a passenger entering or leaving a vehicle, mobile wand 700, provided in the vehicle and powered through a vehicle power outlet (accessory power supply, cigarette lighter, etc.) or a mobile battery unit, may be used to disinfect surfaces and air within the vehicle passenger compartment by application of light as noted herein. In some examples, it is contemplated that the mobile wand 700 will be connected to a wireless network such that mobile wand 700 may operable via a wireless connection.

Figure 8A:
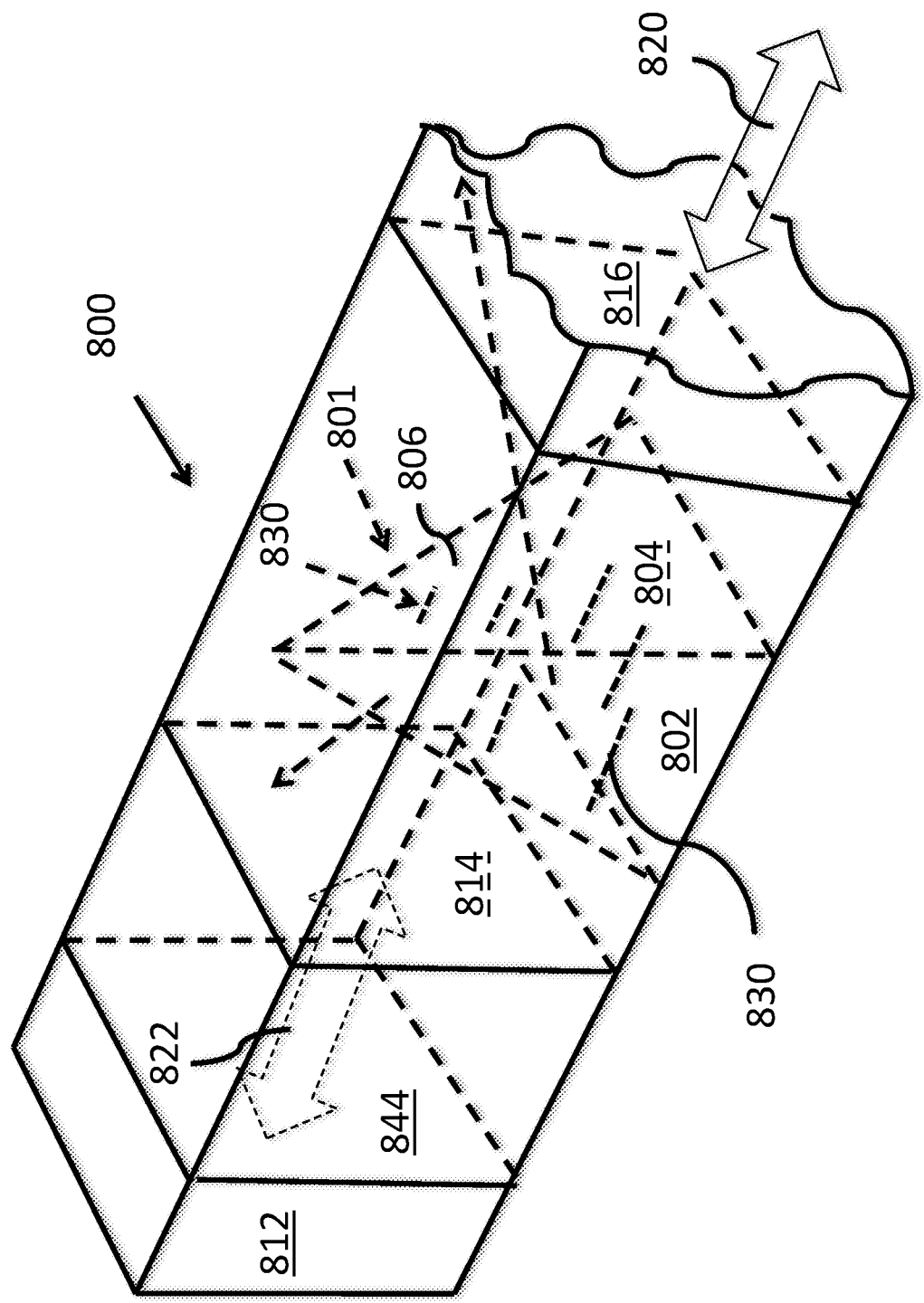
FIG. 8a illustrates a perspective view of a UV radiation system for cleaning viruses from the air in a heating, ventilation, and air conditioning (HVAC) duct such as may be found in an aircraft or a building.

FIG. 8a illustrates a perspective view of UV radiation system 800 for cleaning viruses from the air in a heating, ventilation, and air conditioning (HVAC) duct such as may be found in a plane or a building, including buildings housing farm animals such as pigs (a potential source of swine flu) and chickens (a potential source of bird flu). A five-side pyramid-shaped structure 801 having mirrored interior sides 802, 804 and 806, which are reflective of UV light, may be positioned in air duct 810 adjacent air filter 812. Sides 814 and 816 of UV radiation system 800 each define a void, along a path, indicated by arrows 820 and 822, through which air may flow. UV radiation system 800 may be defined by sides 814, 816 and pyramid-shaped structure 801. One or more UV light sources 830 (shown as dashed lines, only two of which are labeled so as not to obscure illustration) may be disposed on sides 802, 804 and 806. UV light sources 830 (some of which are not labeled for ease of illustration) may be powered by a remote source (not shown) and in some examples UV light sources may be powered wirelessly by the remote source. Panels 840 and 844, which may absorb UV light, abut sides 814 and 816. Depending upon the frequency and intensity of the UV light used, it may be advantageous to restrict irradiation of surfaces beyond that deemed necessary to achieve the task of viral air cleaning.

Figure 8B:
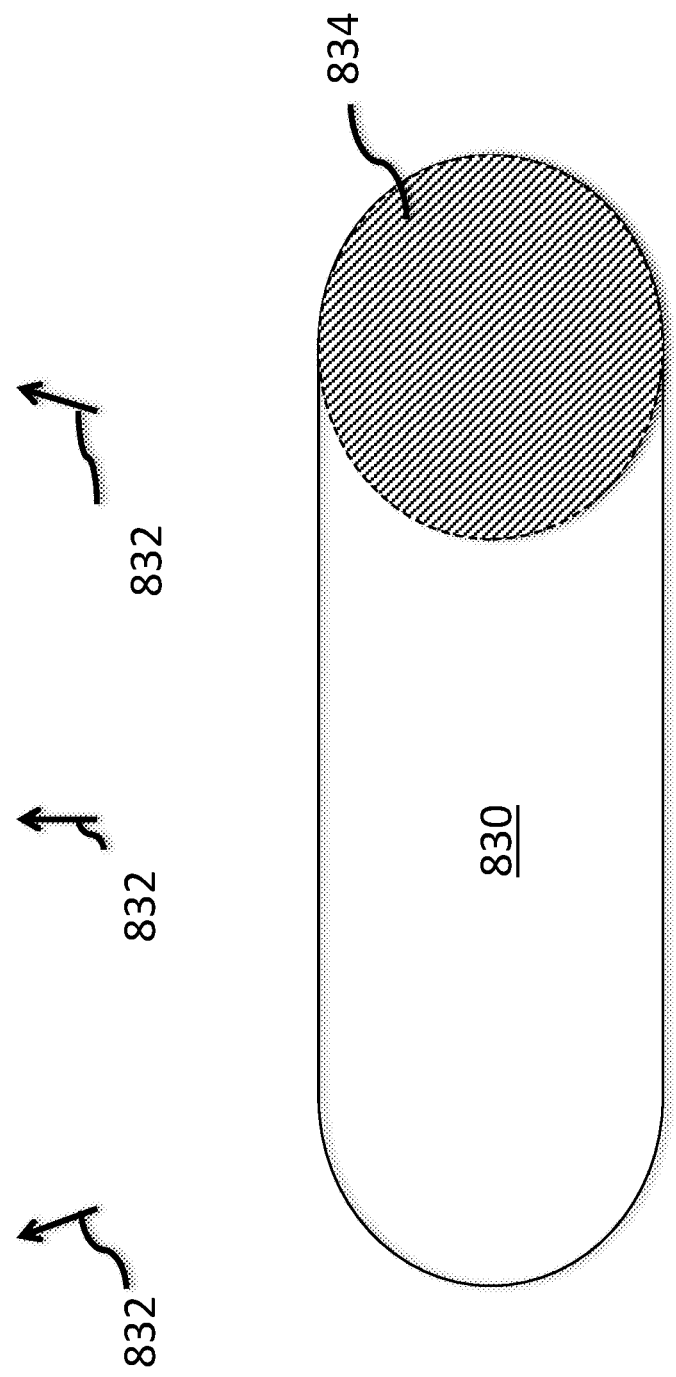

FIG. 8b illustrates a perspective view of UV light source 830 as shown in FIG. 8a. Arrows 832 represent light emanating from UV light source 830. Block 834, which may be a coating on UV light source 830 or a barrier near UV light source 830, serves to block UV radiation from traveling down air duct 810 (FIG. 8a).

Figure 9:
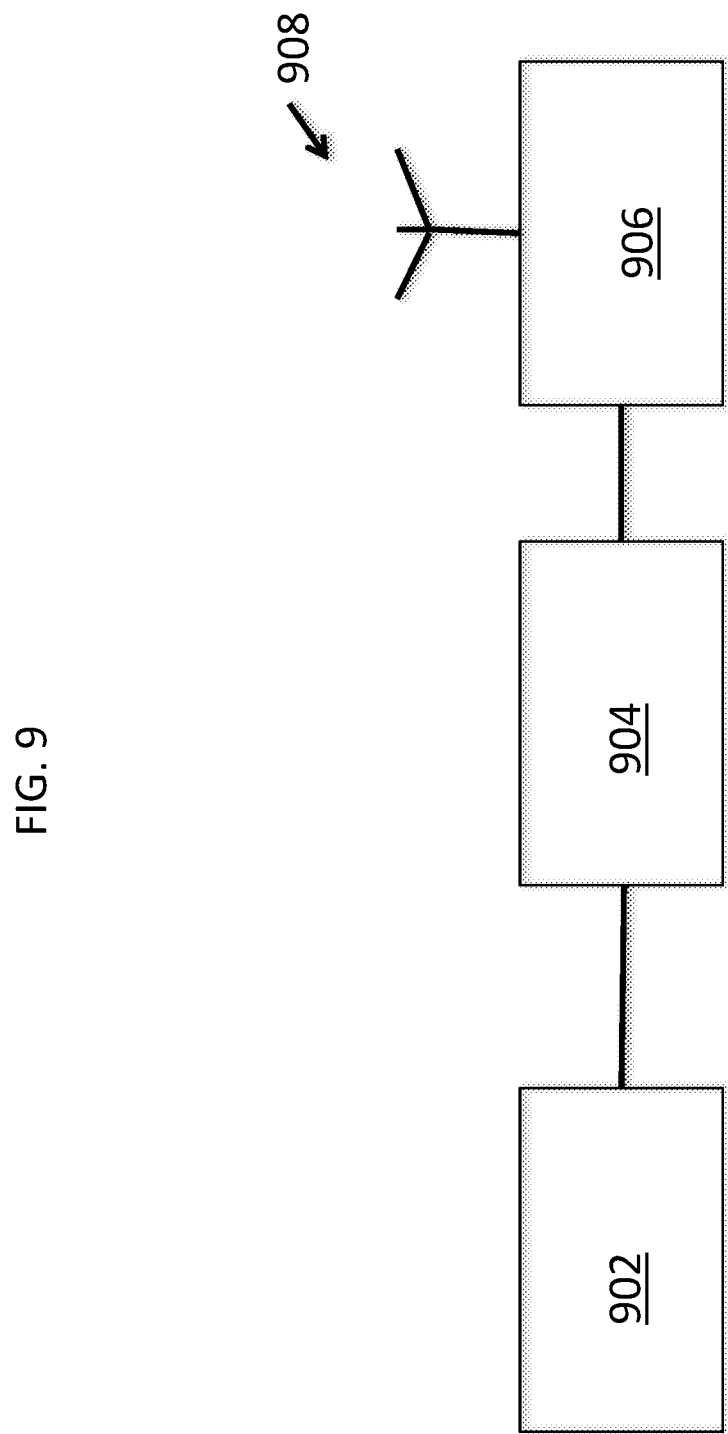
FIG. 9 illustrates a block diagram of a cleaning system for the collection of cleaning data.
Figure 10:
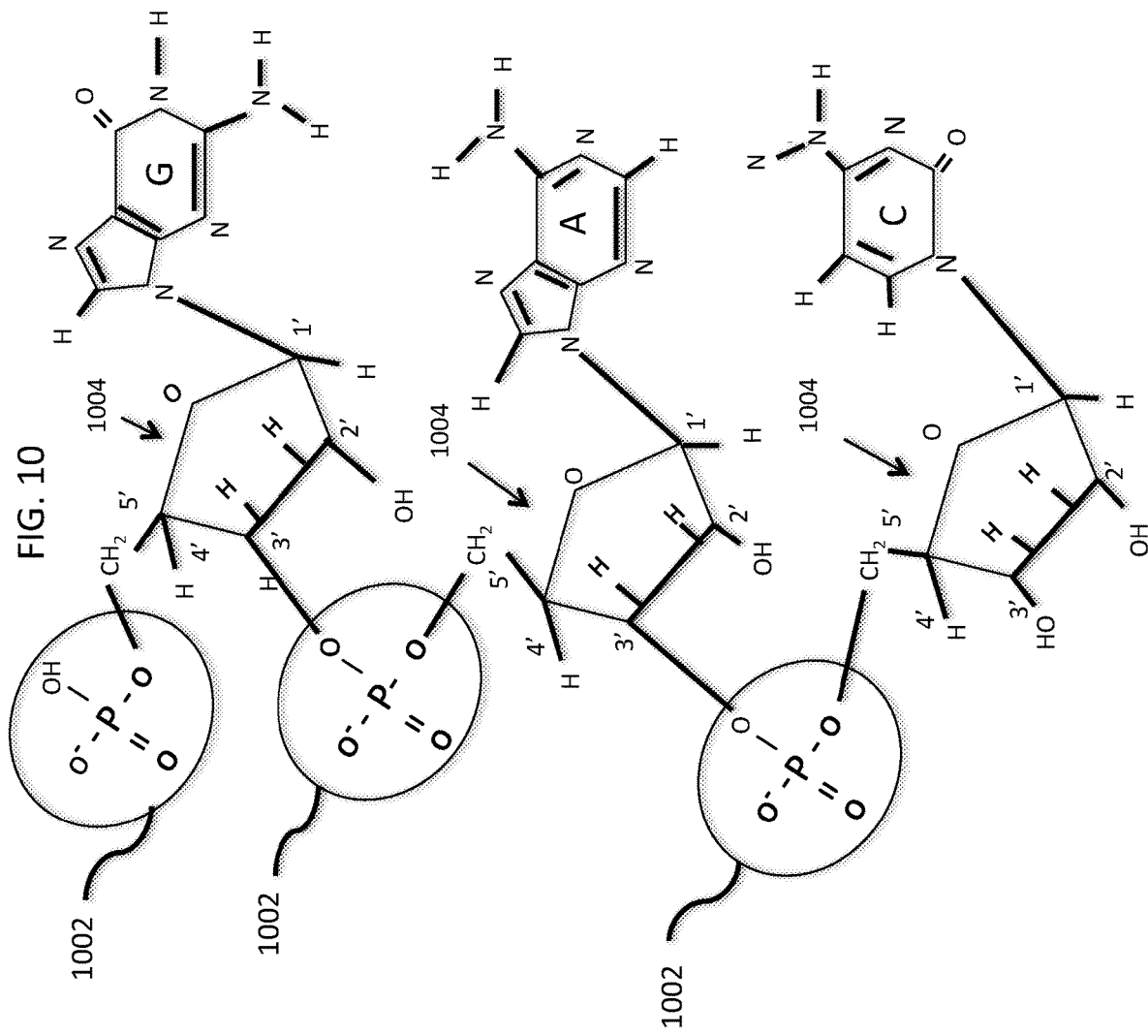
FIG. 10 illustrates a partial strand of a RNA polynucleotide chain.

The foregoing apparatus and method(s) permit a system for collecting reliable cleaning data evidencing comprehensive cleaning of surface. FIG. 9 illustrates a block diagram of a cleaning system for the collection of cleaning data in connection with the foregoing. Memory 902 may store data in connection with cleaning regimens, cleaning records etc. Processor 904, coupled to memory 902, may be programmed to process cleaning data for storage on memory 904. Processor 904 may be coupled to communication device 906 (which may be a transceiver or a transmitter and separate receiver). Processor 904 may programmed to also cause data to be transmitted and received by communication device 906, in connection with antenna 908, regarding cleaning regimens, operations and records. The records may include one or more maps documenting the areas cleaned using the foregoing methods. Cleaning information, including cleaning records may be stored in memory 904. Further, this cleaning information may be shared, with one or more remote locations, as directed through processor 904 using communication device 906, in conjunction with antenna 908.

Experiments exposing viruses to different light wavelengths show that UV-C is the most effective frequency range to inactivate viruses. This may provide insight into why UV-C light has been shown to have greater effect on viral inactivation as compared with other UV frequencies.

There are three basic incident photon interactions with an atom:
 1. Absorption,
 2. elastic (Rayleigh) scattering, or
 3. non-elastic (e.g., Raman or Stokes-Raman) scattering.

While elastic and non-elastic scattering may involve either no or only partially momentum being transferred to an electron, absorption involves a photon being "consumed"

(i.e., absorbed) in its entirety by an electron, causing the electron to "jump" to a more energetic orbital, thereby putting an associated atom/molecule in an excited state. An electron cannot absorb just any photon. The photon has to have an energy equal to the energy difference between the two orbitals between which the electron jumps.

For wave phenomena such as light it is known that:

$$c=\lambda\omega,$$

where c=speed of light, λ=wavelength, and ω=frequency. Note that since c=constant, increasing λ decreases ω and vice versa.

The energy for a light particle or photon is $$E=h\omega, \text{ where } h=\text{Planck's Constant, or} \qquad 1)$$

$$E=hc/\lambda, \qquad 2)$$

Through photolysis, the separation of molecules by the action of light, virions may be destroyed using light at specific wavelengths to produce photons that will break specific molecular bonds (covalent bonds) in an RNA genome. Inactivation of RNA or DNA can be accomplished by targeting specific bonds for photolysis at the corresponding light wavelength to the bond energy for the bond sought to be broken. Stated otherwise, a photolysis effect may be produced by application of light having a wavelength only no greater than and proximate to a wavelength corresponding to the bond energy (hereinafter referred to as the bond energy wavelength) of a chemical bond in a genetic molecule. Bond energies may be calculated from equation 2) (E=hc/λ) through experimental data in determining bond breaking wavelengths. Bond energies have been determined for a number of common bonds. Knowing the bond energy of a bond permits one to calculate the wavelength, λ, (or frequency, w) of the lowest energy light that can break the bond according to λ=hc/E with E (shown above as the relativistic energy) representing the bond energy. 260 nm has been determined to be an effective UV-C wavelength to cause inactivation of some viruses.

Although the primary mechanism for viral inactivation of RNA or DNA has been generally identified as occurring through dimerization, photolysis, the separation of molecules by the action of light, may provide a reliable means by which to destroy virions. It is proposed that viral RNA or DNA may be destroyed using light at specific wavelengths to produce photons that will break specific molecular bonds (covalent bonds) throughout a RNA or DNA genome. The inactivation of a virus may be accomplished by targeting specific bonds for photolysis at the light wavelength corresponding to that equal to or greater than the bond energy for the bond sought to be broken. Bond energies are available for a number of common bonds. Knowing the bond energy of a bond permits one to calculate the wavelength, λ, (or frequency, w) of the lowest energy light that can break the bond according to λ=hc/E with E (the relativistic energy) representing the bond energy. While 260 nm has been determined to be an effective UV-C wavelength to cause inactivation, through dimerization, of some viruses, it is a wavelength corresponding to the bond energy, 459 kilo Joules (kJ)/mole, which is also necessary to break the covalent bond between hydrogen (H) and oxygen (O) atoms.

FIG. 10 illustrates a partial strand of a RNA polynucleotide chain of, for instance, SARS-CoV-2. Given the 26 to 32 kilobases in such a virus, there may be many hydroxyl (—OH) groups and HO in the RNA genome which occur significantly at the 3' and 5' positions. A sugar backbone for an RNA chain is formed by phosphate groups 1002 attaching from the 5' position carbon to the 3' position carbon of the ribose sugars 1004 which attach at the 1' position to a given base such as Guanine (G), Adenine (A) or Cytosine (C). Not shown in the FIG. 10 is a fourth base, found in RNA, designated Uracil (U). In contrast, DNA includes the bases G, A, C and Thymine (T). Various bonds are shown in FIG. 10 which are labeled according to commonly known nomenclature. There are a preponderance of hydroxyl (OH) groups in an RNA genome which occur in an RNA chain which is formed in connection with a base (adenine, uracil, guanine, and cytosine) attaching to a phosphate group and a ribose sugar. With an approach aimed at breaking several different bonds in an RNA strand, it may be possible to design an effective viral disinfection solution that inactivates a virus which minimizes exposure to unnecessary and possibly harmful UV spectra. It is conceivably possible to determine methodologies that which will break every bond in an RNA strand (or DNA strand). Lessening the use of UV radiation at frequencies which are ineffective at viral inactivation or are more than necessary for viral inactivation is a goal as UV radiation may be harmful to human beings, pets, etc. For instance, carbon (C) and oxygen (O) bonds may be targeted. These bonds require at least about 358 kJ/mol of bond energy[23] which corresponds to a UV-B wavelength light of around 334 nm to break the C—O bond. Carbon (C)-Carbon (C) bonds may be targeted. C—C bonds have a bond energy of around 346 kJ/mole requiring a corresponding light of UV-B wavelength of at least around 346 nm to break the C—C bond. Carbon (C)-nitrogen (N) bonds may be targeted. C—N bonds have a bond energy of around 305 kJ/mol, requiring a corresponding light of a UV-A wavelength of at least around 392 nm to break the C—N bond.

Irradiating virions with specific narrow ranges of light that correspond to the frequencies of light at or slightly above (wavelengths of light at or slightly below) that needed to liberate an electron from a bond, may make it possible to inactivate a virion through destruction of the viral RNA. In addition, it may be possible to inactivate a virion through destruction of the viral envelope (of an enveloped RNA virion/virus) by application of heat to the envelope. Although destruction of the viral envelope is primarily contemplated as resulting from application of infrared (IR) light of a sufficient intensity it is also contemplated that heat may also be transmitted to the viral envelope, through application of UV light, sufficient to cause destruction of the viral envelope.

Where a non-laser UV source is used, it may be desirable to use one or more band-pass filters on the produced continuous wavelength UV light to provide only the frequencies related to the targeted nucleotide bonds to the target viruses, bacteria, spores or other biological agents. That is, the foregoing may have a first light source producing a continuous wavelength UV light and may further have one or more band-pass filters that transmit only the frequencies of UV light correlating with targeted bonds of the genetic molecules of targeted biological agents. Thus, by way of example, the foregoing may include a band-pass filter that transmits light having a wavelength corresponding to the bond energy of a chemical bond in a genetic molecule, with the chemical bond being selected from the group consisting of: hydrogen (H)-oxygen (O), carbon (C)-oxygen (O), carbon (C)-carbon (C), carbon (C)-nitrogen (N), or phosphorus (P)-oxygen (O). Additional band-pass filters may be provided to target additional bonds. Multiple individual band-pass filters may be utilized or where appropriate such band-pass filters may be incorporated into a single unit. By utilizing such filters the level of potential human exposure to UV radiation can be minimized. Further, in some examples, targeting molecular bonds which correspond to bond energies for UV irradiation at frequencies lower than (wavelengths longer than) that of UV-C, provides an advantage which may allow safe application of UV light in an environment while living beings are present.

To further enhance the safe use of the present apparatus/system, known or hereafter developed object recognition systems, inclusive of facial recognition systems, may be utilized alone or in conjunction with motion sensors to reduce the possibility of the apparatus/system being operated in the presence of human or animal life.

Through irradiating, simultaneously or in sequence, virions with UV light of specific narrow ranges of frequencies/wavelengths that correspond to the UV light needed to attain absorption by an electron, it may be possible to inactivate a virion through disruption of the viral RNA. In addition, it may be possible to destroy the viral envelope of an enveloped RNA virion/virus through application of heat to the envelope. Although heat may be transmitted to the viral envelope through application of UV light, it contemplated that application of infrared (IR) light of a sufficient intensity may result in viral inactivation. Irradiation may be accomplished in connection with using one or more lasers and or one or more sources which generate irradiation/light isotropically. In one example, the wavelength of light produced may, for instance, be equal to or less than 15 nanometers of a respective selected bond energy or within even narrower ranges such as equal to or less than 10 nanometers, equal to or less than 8 nanometers or equal to or less than 5 nanometers of the wavelength corresponding to that of the respective bond energy. One or more reflectors, proximate to, or remote from, a light source (laser, isotropic light, etc.) may be used to further direct light or disperse light.

The simultaneous irradiation of surfaces or spaces (including air spaces) at around targeted frequencies of light corresponding to specific bond energies, may result in the most effect use of UV irradiation for a known viral genome in order to inactivate a virion through RNA (or DNA) strand disruption/destruction. Further, irradiation of open spaces surfaces at around targeted frequencies of light, corresponding to specific bond energies, may result in inactivation of a RNA strand existing in air. The devices and systems disclosed herein may be used to deliver such irradiation. More specifically, the foregoing devices and systems may be used connection with IR irradiation of surfaces and spaces, in a manner which is intended to disrupt/destruct the viral envelope, thereby rendering the spike protein ineffective. The foregoing may offer an advantage in allowing disinfection to occur without resorting to use of UV-C frequencies and/or allowing use of more efficient methods of disinfection that do not produce radiation which, to a great extent, is unnecessary or ineffective.

Irradiating molecular bonds at a specific wavelength/frequency to cause viral inactivation is also a function of the intensity of that irradiation. Thusly, the production of photons may be increased, in connection with increased intensity. Increasing the number of photons of the desired frequency increases the likelihood that a bond-breaking interaction will occur. The photons which may be absorbed by electrons in molecular bonds may result in a sufficiently significant number of broken bonds to cause viral inactivation.

The foregoing may be accomplished through software code running in one or more processors on a communication device in conjunction with a processor in a server running complementary software code.

It is appreciated that in order to practice the method of the foregoing as described above, it is not necessary that the processors and/or the memories of the processing machine be physically located in the same geographical place. That is, each of the processors and the memory (or memories) used by the processing machine may be located in geographically distinct locations and connected so as to communicate in any suitable manner. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated that the processor may be two pieces of equipment in two different physical locations. The two distinct pieces of equipment may be connected in any suitable manner. Additionally, the memory may include two or more portions of memory in two or more physical locations.

To explain further, processing, as described above, is performed by various components and various memories. However, it is appreciated that the processing performed by two distinct components as described above may, in accordance with a further embodiment of the foregoing, be performed by a single component. Further, the processing performed by one distinct component as described above may be performed by two distinct components. In a similar manner, the memory storage performed by two distinct memory portions, as described above, may, in accordance with a further embodiment of the foregoing, be performed by a single memory portion. Further, the memory storage, performed by one distinct memory portion, as described above, may be performed by two memory portions.

Further, various technologies may be used to provide communication between the various processors and/or memories, as well as to allow the processors and/or the memories of the foregoing to communicate with any other entity, i.e., so as to obtain further instructions or to access and use remote memory stores, for example. Such technologies used to provide such communication might include a network, the Internet, Intranet, Extranet, LAN, an Ethernet, wireless communication via cell tower or satellite, or any client server system that provides communication, for example. Such communications technologies may use any suitable protocol such as TCP/IP, UDP, or OSI, for example.

As described above, a set of instructions may be used in the processing of the foregoing. The set of instructions may be in the form of a program or software. The software may be in the form of system software or application software, for example. The software might also be in the form of a collection of separate programs, a program module within a larger program, or a portion of a program module, for example. The software used might also include modular programming in the form of object-oriented programming. The software may instruct the processing machine what to do with the data being processed.

Further, it is appreciated that the instructions or set of instructions used in the implementation and operation of the foregoing may be in a suitable form such that the processing machine may read the instructions. For example, the instructions that form a program may be in the form of a suitable programming language, which is converted to machine language or object code to allow the processor or processors to read the instructions. That is, written lines of programming code or source code, in a particular programming language, are converted to machine language using a compiler, assembler or interpreter. The machine language is binary coded machine instructions that are specific to a particular type of processing machine, i.e., to a particular type of computer, for example. The computer understands the machine language.

Any suitable programming language may be used in accordance with the various embodiments of the foregoing. Illustratively, the programming language used may include assembly language, Ada, APL, Basic, C, C++, COBOL, dBase, Forth, Fortran, Java, Modula-2, Pascal, Prolog, REXX, Visual Basic, and/or JavaScript, for example. Further, it is not necessary that a single type of instruction or single programming language be utilized in conjunction with the operation of the system and method of the foregoing. Rather, any number of different programming languages may be utilized as is necessary and/or desirable.

Also, the instructions and/or data used in the practice of the foregoing may utilize any compression or encryption technique or algorithm, as may be desired. An encryption module might be used to encrypt data. Further, files or other data may be decrypted using a suitable decryption module, for example.

As described above, the foregoing may illustratively be embodied in the form of a processing machine, including a computer or computer system, for example, that includes at least one memory. It is to be appreciated that the set of instructions, i.e., the software for example, that enables the computer operating system to perform the operations described above may be contained on any of a wide variety of media or medium, as desired. Further, the data that is processed by the set of instructions might also be contained on any of a wide variety of media or medium. That is, the particular medium, i.e., the memory in the processing machine, utilized to hold the set of instructions and/or the data used in the foregoing may take on any of a variety of physical forms or transmissions, for example. Illustratively, the medium may be in the form of paper, paper transparencies, a compact disk, a DVD, an integrated circuit, a hard disk, a floppy disk, an optical disk, a magnetic tape, a RAM, a ROM, a PROM, an EPROM, a wire, a cable, a fiber, a communications channel, a satellite transmission, a memory card, a SIM card, or other remote transmission, as well as any other medium or source of data that may be read by the processors of the foregoing.

Further, the memory or memories used in the processing machine that implements the foregoing may be in any of a wide variety of forms to allow the memory to hold instructions, data, or other information, as is desired. Thus, the memory might be in the form of a database to hold data. The database might use any desired arrangement of files such as a flat file arrangement or a relational database arrangement, for example.

In the system and method of the foregoing, a variety of "user interfaces" may be utilized to allow a user to interface with the processing machine or machines that are used to implement the foregoing. As used herein, a user interface includes any hardware, software, or combination of hardware and software used by the processing machine that allows a user to interact with the processing machine. A user interface may be in the form of a dialogue screen for example. A user interface may also include any of a mouse, touch screen, keyboard, keypad, voice reader, voice recognizer, dialogue screen, menu box, list, checkbox, toggle switch, a pushbutton or any other device that allows a user to receive information regarding the operation of the processing machine as it processes a set of instructions and/or provides the processing machine with information. Accordingly, the user interface is any device that provides communication between a user and a processing machine. The information provided by the user to the processing machine through the user interface may be in the form of a command, a selection of data, or some other input, for example.

As discussed above, a user interface is utilized by the processing machine that performs a set of instructions such that the processing machine processes data for a user. The user interface is typically used by the processing machine for interacting with a user either to convey information or receive information from the user. However, it should be appreciated that in accordance with some embodiments of the system and method of the foregoing, it is not necessary that a human user actually interact with a user interface used by the processing machine of the foregoing. Rather, it is also contemplated that the user interface of the foregoing might interact, i.e., convey and receive information, with another processing machine, rather than a human user. Accordingly, the other processing machine might be characterized as a user. Further, it is contemplated that a user interface utilized in the system and method of the foregoing may interact partially with another processing machine or processing machines, while also interacting partially with a human user.

While the discussion herein has focused on the novel coronavirus, the foregoing will also find application relative to other biological agents, such as other viruses, bacteria, or spores. As such, it will be understood that the genetic material contained in such biological agents will include nucleotide chains of varying lengths. Such disparate nucleotide chain lengths may call for varying UV intensities in order to achieve inactivation thereof and such variation is within the scope of the present disclosure.

The foregoing has been described herein using specific embodiments for the purposes of illustration only. It will be readily apparent to one of ordinary skill in the art, however, that the principles of the foregoing can be embodied in other ways. While use of the present apparatus has been described with regard to viruses, it is contemplated that it would be similarly effective in use against biological agents in general including bacteria and spores wherein specific bonds, as discussed herein, are targeted by the apparatus. Further, the foregoing may be effective against nerve agents such as sarin or other gas agents, e.g., mustard, tear, etc. Therefore, the foregoing should not be regarded as being limited in scope to the specific embodiments disclosed herein, but instead as being fully commensurate in scope with the following claims.

We claim:

1. An apparatus for use in an environment where living beings may be present, the apparatus being configured for viral inactivation and comprising:

at least one light source, the at least one light source being configured to produce, simultaneously, ultraviolet (UV) light and infrared (IR) light, the UV light being sufficient to cause viral inactivation through genetic bond-breaking, and the IR light being sufficient to heat a viral membrane so as to cause viral inactivation through viral membrane degradation;

a first band-pass filter being configured to transmit UV light, produced by the at least one light source, of a first wavelength only no greater than and proximate to a first bond energy wavelength corresponding to a bond energy of a first chemical bond in a genetic molecule, the first chemical bond being selected from the group consisting of hydrogen-oxygen, carbon-oxygen, carbon-carbon, carbon-nitrogen, and phosphorus-oxygen; and a second band-pass filter being configured to transmit UV light, produced by the at least one light source, of a second wavelength only no greater than and proximate to a second bond energy wavelength corresponding to a bond energy of a second chemical bond in a genetic molecule, the second chemical bond being selected from the group consisting of hydrogen-oxygen, carbon-oxygen, carbon-carbon, carbon-nitrogen, and phosphorus-oxygen, the first and second wavelengths being distinct from each other, wherein the apparatus is configured to safely inactivate viruses in an environment when living beings are present in the environment.

2. The apparatus of claim 1 further comprising a third band-pass filter being configured to transmit UV light, produced by the at least one light source, of a third wavelength only no greater than and proximate to a third bond energy wavelength corresponding to a bond energy of a third chemical bond in a genetic molecule, the third chemical bond being selected from the group consisting of hydrogen-oxygen, carbon-oxygen, carbon-carbon, carbon-nitrogen, and phosphorus-oxygen, wherein the first, second, and third wavelengths are distinct from each other.

3. The apparatus of claim 1, further comprising:
a housing, the at least one light source being at least partially contained within the housing, the at least one light source being selected from the group consisting of an incandescent light source, a laser light source, a light emitting diode (LED) source, a liquid crystal display (LCD) diode source and combinations thereof and wherein the first wavelength is equal to or less than 15 nanometers of the first bond energy wavelength and wherein the second wavelength is equal to or less than 15 nanometers of the second bond energy wavelength.

4. The apparatus of claim 3, further comprising a controller for controlling the at least one light source.

5. The apparatus of claim 3, wherein the laser light is selected from the group consisting of a continuous-mode operating laser, a pulsed-mode operating laser and a combination thereof.

6. The apparatus of claim 1, further comprising:
a control unit having a processor, the processor controlling the sources of IR and UV radiation;
a temperature sensor coupled to the control unit and being operable to detect the temperature of a surface upon which the temperature sensor is directed;
a positioning apparatus being operable to independently position the source of IR radiation, the source of UV radiation, and the temperature sensor; and
a vehicle coupled to the positioning apparatus.

7. An apparatus as recited in claim 1 further comprising a third band-pass filter being configured to transmit light, produced by the source of UV radiation, of a third wavelength only no greater than and proximate to a third bond energy wavelength corresponding to a bond energy of a third chemical bond in a genetic molecule, the third chemical bond being selected from the group consisting of hydrogen-oxygen, carbon-oxygen, carbon-carbon, carbon-nitrogen, and phosphorus-oxygen, wherein the first, second, and third wavelengths are distinct from each other.

8. The apparatus as recited in claim 6, further comprising a system selected from the group consisting of a camera system coupled to the control unit, an object recognition system coupled to the control unit, a motion detection system coupled to the control unit and a combination thereof.

* * * * *